(12) United States Patent  
Langemann et al.

(10) Patent No.: US 6,815,563 B2
(45) Date of Patent: Nov. 9, 2004

(54) METHOD FOR PRODUCING BICYCLIC 1,3-DIKETONES

(75) Inventors: Klaus Langemann, Schauenburg (DE);
Ulf Misslitz, Neustadt (DE); Ernst Baumann, Dudenhofen (DE);
Wolfgang von Deyn, Neustadt (DE);
Steffen Kudis, Mannheim (DE);
Thorsten Volk, Mannheim (DE);
Guido Mayer, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/332,034

(22) PCT Filed: Jul. 4, 2001

(86) PCT No.: PCT/EP01/07639
§ 371 (c)(1),
(2), (4) Date: Jan. 6, 2003

(87) PCT Pub. No.: WO02/06197
PCT Pub. Date: Jan. 24, 2002

(65) Prior Publication Data
US 2003/0187290 A1 Oct. 2, 2003

(30) Foreign Application Priority Data
Jul. 6, 2000 (DE) .......................... 100 32 396

(51) Int. Cl.⁷ ............................... A01N 43/58
(52) U.S. Cl. ..................... 568/327; 568/31; 568/42; 568/43; 568/304; 504/236; 504/237; 504/238; 504/296; 504/348
(58) Field of Search ................. 568/327, 304, 568/31, 42, 43; 504/236, 237, 238, 296, 348

(56) References Cited
U.S. PATENT DOCUMENTS
5,536,703 A 7/1996 Lee et al.

(List continued on next page.)

FOREIGN PATENT DOCUMENTS
EP 338 992 10/1989

(List continued on next page.)

OTHER PUBLICATIONS
JP 09052807—Derwent.

(List continued on next page.)

Primary Examiner—Sabiha Qazi
(74) Attorney, Agent, or Firm—Keil & Weinkauf

(57) ABSTRACT

A process for preparing bicyclic 1,3-diketones of the formula I

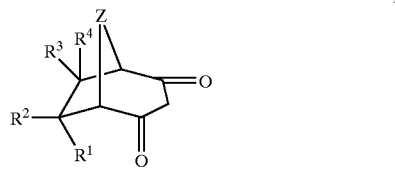

where
$R^1$, $R^2$, $R^3$ and $R^4$ are hydrogen, $C_1$–$C_4$-alkyl, $C_1$–$C_4$-alkoxy-carbonyl, halogen, cyano, nitro, $C_1$–$C_4$-alkylthio, $C_1$–$C_4$-alkylsulfenyl or $C_1$–$C_4$-alkylsulfonyl and
Z is $C_1$–$C_4$-alkylene, O, S, N—$R^5$ where
$R^5$ is $C_1$–$C_4$-alkyl or $C_1$–$C_4$-alkylcarbonyl,
which comprises
a) reacting a bicyclic olefin of the formula II with haloform in the presence of a base to give the ring-expanded product of the formula III

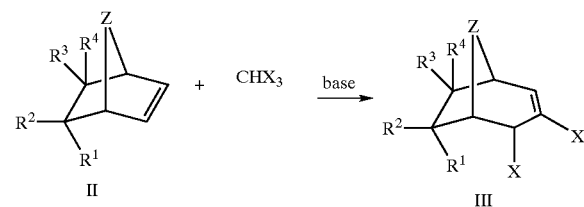

where
$R^1$–$R^4$ and Z are as defined above and
X is halogen;
b) hydrolyzing the allylic halogen of the compound of the formula III to the allyl alcohol of the formula IV

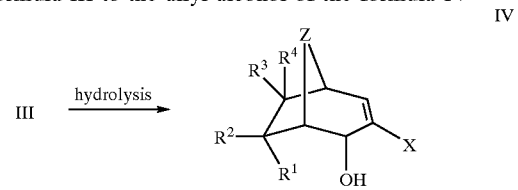

c) oxidizing the allyl alcohol of the formula IV to the unsaturated ketone of the formula V

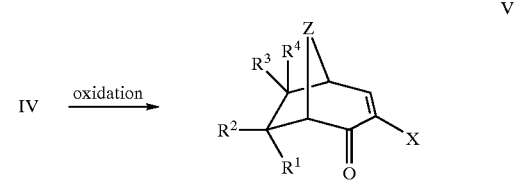

d) reacting the ketone of the formula V with a nucleophilic ion $Y^-$ which stabilizes a negative charge to give the ketone of the formula VI

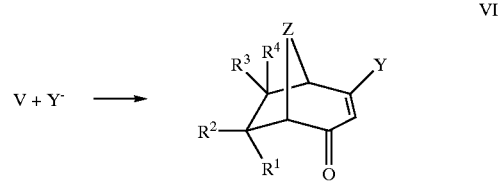

e) hydrolyzing the ketone of the formula VI to the bicyclic 1,3-diketone of the formula I,
novel intermediates and novel processes for preparing these intermediates are described.

19 Claims, No Drawings

U.S. PATENT DOCUMENTS 5,608,101 A    3/1997   Lee et al.
5,801,120 A *  9/1998   Lee et al.

FOREIGN PATENT DOCUMENTS

| JP | 9/52807   | 2/1997  |
| JP | 10/265415 | 10/1998 |
| JP | 10/265441 | 10/1998 |

OTHER PUBLICATIONS

Bull.Soc.Chim.Fr. 1975, 7–8 1691–1698, Cheminat et al.
Durocher et al.,XP–001022681, 260–267, 1964.
Gleiter et al., XP–001026048, 655–659, 1980.
JP 10265441—Derwent.
JP 1025615—Derwent.
Chem. Ber. 1936, 69, 1199, Guha et al.
Durocher et al, 260–267, Can.J.of Chem. vol. 42 (1964).

* cited by examiner

METHOD FOR PRODUCING BICYCLIC 1,3-DIKETONES

The present invention relates to a process for preparing bicyclic 1,3-diketones of the formula I,

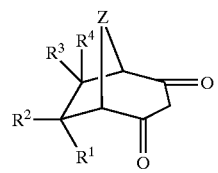

where $R^1$, $R^2$, $R^3$ and $R^4$ are hydrogen, $C_1$–$C_4$-alkyl, $C_1$–$C_4$-alkoxycarbonyl, halogen, cyano, nitro, $C_1$–$C_4$-alkylthio, $C_1$–$C_4$-alkylsulfenyl or $C_1$–$C_4$-alkylsulfonyl and Z is $C_1$–$C_4$-alkylene, O, S, N—$R^5$ where $R^5$=$C_1$–$C_4$-alkyl or $C_1$–$C_4$-alkylcarbonyl, novel intermediates and novel processes for preparing these intermediates.

Bicyclic 1,3-diketones are useful compounds which can be employed as intermediates in crop protection. U.S. Pat. No. 5,608,101, U.S. Pat. No. 5,536,703, JP 09052807, JP 10265441 and JP 10265415, for example, disclose bicyclooctanediones as intermediates for herbicidally active compounds.

The processes disclosed in JP 10 265 441 and JP 10 256 415 use highly expensive norbornanone as starting material. Owing to the high costs of the starting materials, these processes do not appear to be economical.

Other syntheses have also been described in the literature. They all suffer from the disadvantage that either a large number of synthetic steps are involved (Chem. Ber. 69 (1936), 1199) or that toxicologically and/or ecologically objectionable reagents are used (Can. J. Chem. 42 (1964), 260; Bull. Soc. Chim. Fr. 7–8 (1975), 1691), so that these syntheses are not acceptable from an industrial point of view.

This application is a 371 of PCT/EP01/07639 filed on Jul. 4, 2001.

It is an object of the present invention to provide an alternative process for preparing bicyclic 1,3-diketones of the formula I, which process does not have the disadvantages of the prior art.

We have found that this object is achieved by a process for preparing bicyclic 1,3-diketones of the formula I

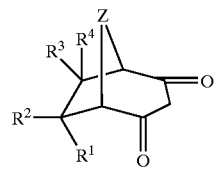

where $R^1$, $R^2$, $R^3$ and $R^4$ are hydrogen, $C_1$–$C_4$-alkyl, $C_1$–$C_4$-alkoxy-carbonyl, halogen, cyano, nitro, $C_1$–$C_4$-alkylthio, $C_1$–$C_4$-alkylsulfenyl or $C_1$–$C_4$-alkylsulfonyl and Z is $C_1$–$C_4$-alkylene, O, S, N—$R^5$ where $R^5$ is $C_1$–$C_4$-alkyl or $C_1$–$C_4$-alkylcarbonyl, which comprises a) reacting a bicyclic olefin of the formula II with haloform in the presence of a base to give the ring-expanded product of the formula III

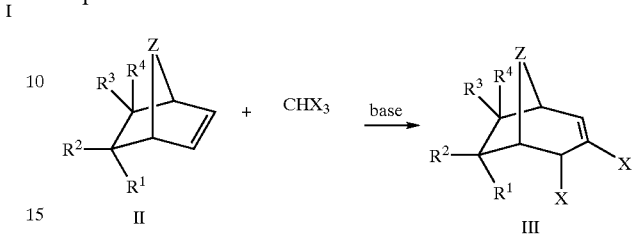

where $R^1$–$R^4$ and Z are as defined above and

X is halogen;

b) hydrolyzing the allylic halogen of the compound of the formula III to the allyl alcohol of the formula IV

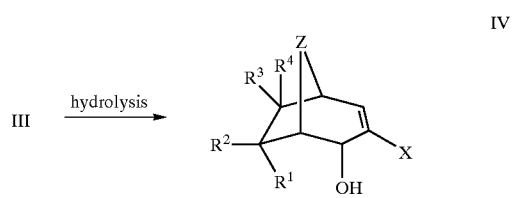

c) oxidizing the allyl alcohol of the formula IV to the unsaturated ketone of the formula V

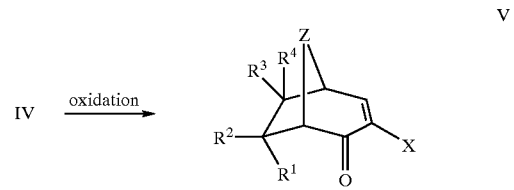

d) reacting the ketone of the formula V with a nucleophilic ion $Y^-$ which stabilizes a negative charge to give the ketone of the formula VI

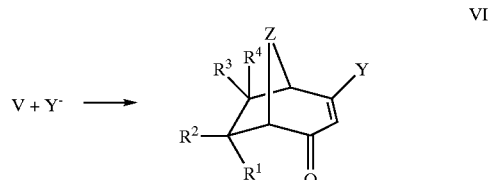

e) hydrolyzing the ketone of the formula VI to the bicyclic 1,3-diketone of the formula I.

Furthermore, it has been found that, bypassing the hydrolysis step b), the allylic halogen of the compound of the formula III can be oxidized to the unsaturated ketone of the formula V.

Moreover, it has been found that the reaction of the ketone of the formula V with a nucleophilic ion $Y^-$, which stabilizes a negative charge, to give the ketone of the formula VI can, without intermediate isolation, be hydrolyzed directly to give the bicyclic 1,3-diketone of the formula I.

Furthermore, we have found intermediates of the formula VI

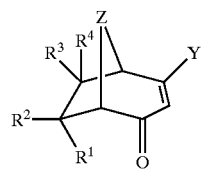

VI where

R$^1$, R$^2$, R$^3$ and R$^4$ are hydrogen, C$_1$–C$_4$-alkyl, C$_1$–C$_4$-alkoxy-carbonyl, halogen, cyano, nitro, C$_1$–C$_4$-alkylthio, C$_1$–C$_4$-alkylsulfenyl or C$_1$–C$_4$-alkylsulfonyl and Z is C$_1$–C$_4$-alkylene, O, S, N—R$^5$ where R$^5$ is C$_1$–C$_4$-alkyl or C$_1$–C$_4$-alkylcarbonyl, Y is cyano, sulfonate, C$_1$–C$_6$-alkylsulfonyl or unsubstituted or C$_1$–C$_3$-alkyl-, C$_1$–C$_3$-alkoxy-, C$_1$–C$_3$-alkylthio-, C$_1$–C$_3$-alkylsulfonyl-, halogen-, cyano-, nitro- or sulfonate-substituted phenylsulfonyl.

Bicyclic 1,3-diketones of the formula I can be present as keto-enol tautomers Ia and Ib. This present invention also relates to a process for preparing tautomers of the formulae Ia and Ib.

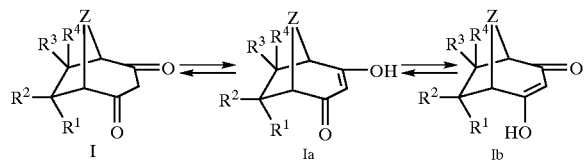

The process according to the invention for preparing compounds I comprises substantially one or more of the process steps a)–e). Also possible are such reaction sequences in which one or more of the process steps a)–e) are combined in one step (one-pot synthesis).

A possible reaction sequence leading to the preparation of the compounds I is compiled in the overview scheme below:

For the sake of clarity, only the synthesis of one enantiomer is described in each case. The process according to the invention also embraces the synthesis of the other enantiomer in each case.

The individual reaction steps are illustrated in more detail below:

Step a):

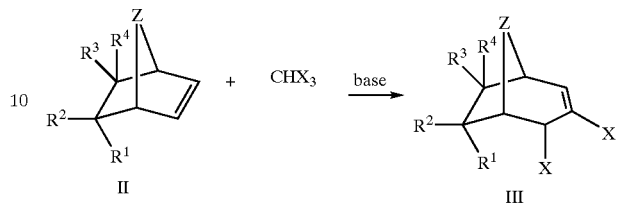

The reaction is carried out, for example, under the following conditions:

This step proceeds via a dihalocarbene, preferably dichlorocarbene, which is generated from haloform and a base.

Haloform, preferably chloroform, is used in the presence of a base, for example an alkali metal hydroxide, an alkaline earth metal hydroxide, an alkali metal alkoxide or an alkali metal amide, preferably NaOH, KOH, sodium methoxide, and, if appropriate, a phase-transfer catalyst, for example tetrabutylammonium chloride, trimethylbenzylammonium chloride or Aliquat 336, in the absence of a solvent or in an inert hydrocarbon or halogenated hydrocarbon, for example hexane, heptane, petroleum ether, dichloromethane, carbon tetrachloride, dichloroethane or chlorobenzene, and, if appropriate, water.

The stoichiometric ratios are, for example, as follows: 1–4 equivalents of haloform, if appropriate 0.0001–0.10 equivalent of phase-transfer catalyst and 1–4 equivalents of base are used per equivalent of the compound II.

The addition is carried out, for example, in the following order: in the inert solvent, compound II and haloform are, if appropriate, admixed with phase-transfer catalyst and, at 0° C.–100° C., preferably 30–60° C., admixed with the base. Work-up is carried out, for example, by stirring the product mixture into water, followed by extraction and, if appropriate, distillation of the resulting residue under reduced pressure. Work-up can also be carried out without purification by distilling off the solvent and using the crude product directly for step b).

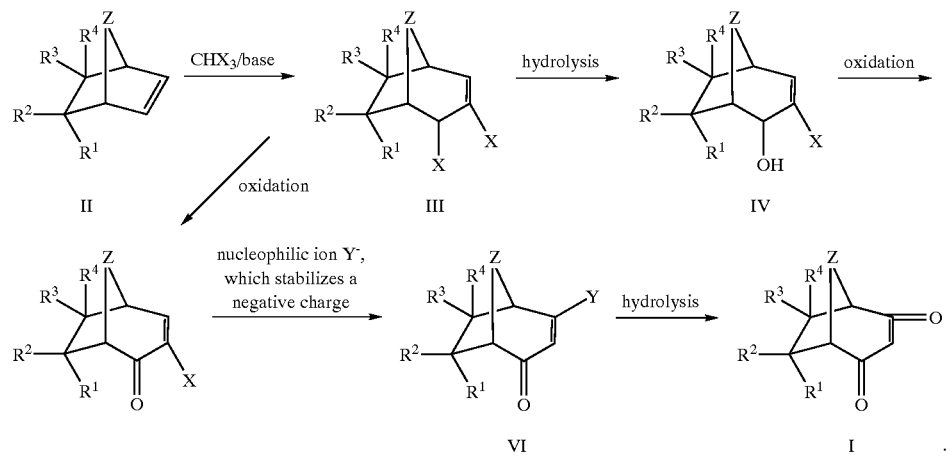

The preparation of exo-3,4-dichlorobicyclo[3.2.1]oct-2-ene has already been described in the literature. However, either the yields are unsatisfactory (J. Am. Chem. Soc. 1954, 6162; J. Org. Chem. 28 (1963), 2210; Recl. Trav. Chim. Pays-Bas 80, (1961) 740) or highly toxic phenyltrichloromethylmercury is used (Helv. Chim. Acta 55 (1972), 790; Org. Synth., Coll. Vol V, 1973, 969). The generation of carbene from ethyl trichloroacetate and base (Org. Synth. Coll. Vol. VI, 1988, 142) is highly exothermic: when this synthesis procedure was repeated, there was product outflow from the apparatus. carbene addition under phase-transfer catalysis is likewise already known in the literature (Houben/Weyl, Methoden der organischen Chemie [Methods of organic chemistry], Vol. E19/b, 1989, 1527, Thieme Verlag, Stuttgart; Synthesis 9 (1972), 485). However, there is still scope for improvement with respect to yield and reaction time. When these procedures were checked, the yields obtained for larger batches were considerably lower. It has been observed that dichlorocarbene reacts with water to give carbon monoxide which, on an industrial scale, represents a potential danger.

Step b):

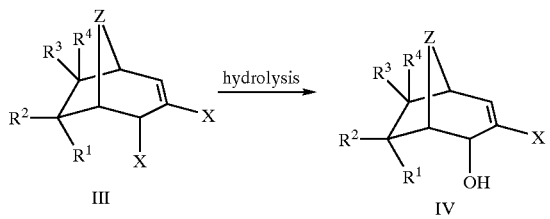

The hydrolysis is carried out, for example, under the following conditions: suitable solvents are water, with or without addition of a phase-transfer catalyst, tetrahydrofuran, dimethylformamide or dimethyl sulfoxide. The hydrolysis is carried out, for example, using alkali metal hydroxides, such as sodium hydroxide or potassium hydroxide, or alkaline earth metal hydroxides, for example magnesium hydroxide or calcium hydroxide; preference is given to NaOH and KOH.

The reaction is carried out at from 0° C. to the boiling point of the solvent, preferably at from room temperature to the reflux temperature of the solvent in question. The stoichiometric ratios are as follows: 1–5 equivalents of base, preferably 1–1.5 equivalents of base, are used per equivalent of the compound III.

Work-up is carried out, for example, by stirring the mixture into water and extracting with an organic solvent and subsequent fractional distillation. If the solvent used is water, extraction can be carried out directly.

The hydrolysis of a cyclic halogen atom has already been described (J. Chem. Soc. Perk. Trans. II, 1982, 39). However, the fact that this reaction takes a very long time (3 days) makes its use unattractive for an industrial synthesis. In another literature reference (Synth. Comm. 24 (1994), 2923), formic acid and selenium dioxide are used to synthesis the compounds IV. However, the high toxicity of selenium compounds excludes this variant, too, from being used in an industrial preparation.

Step c):

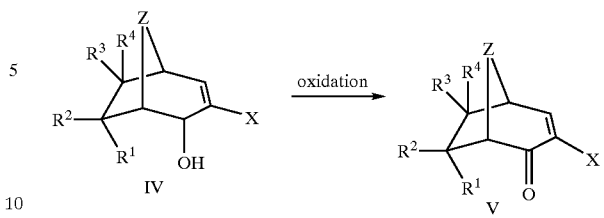

The oxidation can be carried out, for example, using the following oxidizing agents: air, manganese dioxide, potassium permanganate, Jones's reagent (chromic acid/sulfuric acid), dimethyl sulfoxide, if appropriate with additives, such as $NaHCO_3$, potassium hydrogenphosphate or potassium dihydrogenphosphate, or activators, such as oxalyl chloride, phosphorus trichloride, phosphorus oxychloride, thionyl chloride, acetyl chloride, acetic anhydride, sulfur trioxide/pyridine complex, tertiary amine oxides, for example trimethylamine oxide or N-methylmorpholine N-oxide, hydrogen peroxide, if appropriate using a catalyst, for example sodium tungstate, sodium hypochlorite, peracids, for example perbenzoic acids, peracetic acid or pertrifluoroacetic acid, bromine, chlorine, ruthenium tetraoxide, if appropriate catalytically with auxiliary oxidants, for example $NaIO_4$, pyridinium dichromate, pyridinium chlorochromate, cerium ammonium nitrate, nitric acid, lead tetraacetate, N-chlorosuccinimide, N-bromosuccinimide, preferably sodium hypochlorite, hydrogen peroxide, if appropriate in the presence of a catalyst, for example sodium tungstate, air, N-chlorosuccinimide or dimethyl sulfoxide with additives, for example potassium hydrogenphosphate/potassium dihydrogenphosphate, or activators, for example oxalyl chloride, thionyl chloride, acetic anhydride or phosphorus trichloride. Suitable solvents are water, inert hydrocarbons, such as hexane, heptane or petroleum ether, or inert chlorinated hydrocarbons, such as dichloromethane or chlorobenzene. If the oxidation agent is a liquid, the use of additional solvents can be dispensed with.

The oxidation is carried out, for example, at from −60° C. to the boiling point of the solvent in question.

In the literature, the synthesis of compounds V from alkoxynorbornenes (Bull. Soc. Chim. Fr. 7–8 (1974), 1638) is described. The only easy way to obtain alkoxynorbornenes is from norbornanone and, owing to the high price of norbornanone, this route is not of any interest for an industrial synthesis.

Combination of Steps b) and c):

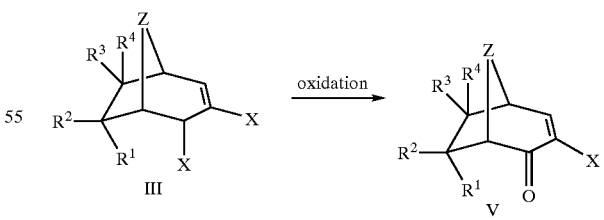

It is also possible to oxidize the allyl chloride III directly to the ketone of the formula V, bypassing step b). Oxidizing agents suitable for this purpose are, for example, air, dimethyl sulfoxide in the presence of additives, for example bases such as sodium bicarbonate or potassium hydrogenphosphate and potassium dihydrogenphosphate, tertiary amine oxides, for example 4-dimethylaminopyridine N-oxide or trimethylamine N-oxide, in inert hydrocarbons, such as hexane, heptane or petroleum ether, or without addition of solvent.

Step d):

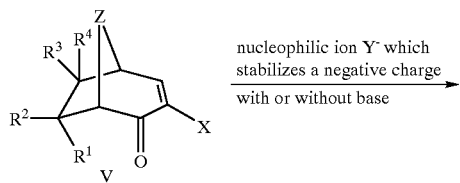

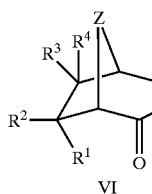

The reaction is carried out, for example, under the following conditions: the solvents used are, for example: polar aprotic solvents, such as dimethylformamide, dimethylacetamide, N-methylpyrrolidone, dimethyl sulfoxide, dimethylpropyleneurea, acetonitrile or propionitrile, polar protic solvents, such as methanol, ethanol, n-propanol, isopropanol or water, if appropriate with addition of a phase-transfer catalyst, ethers, such as diethyl ether, dibutyl ether, diisopropyl ether, tetrahydrofuran, dioxane or methyl tert-butyl ether, halogenated hydrocarbons, such as dichloromethane, chloroform, carbon tetrachloride, dichloroethane or chlorobenzene, aromatic compounds, such as benzene, toluene, xylene or nitrobenzene, ketones, such as acetone, butanone or methyl isobutyl ketone, or carboxylic esters, such as ethyl acetate. Preference is given to using, as solvents, alcohols, acetonitrile, dichloromethane and acetone. The reaction is carried out at from −40° C. to 150° C., preferably at from room temperature to the reflux temperature of the solvent in question. Suitable nucleophilic ions which stabilize a negative charge are, eg, cyanides, sulfites, $C_1$–$C_6$-alkylsulfinates or unsubstituted or $C_1$–$C_3$-alkyl-, $C_1$–$C_3$-alkoxy-, $C_1$–$C_3$-alkylthio-, $C_1$–$C_3$-alkylsulfonyl-, halogen-, cyano-, nitro- or sulfonate-substituted phenylsulfinate and mixtures thereof. Sources of cyanide can be, for example, hydrocyanic acid, alkali metal cyanides, such as lithium cyanide, sodium cyanide or potassium cyanide, or organic compounds, trimethylsilyl cyanide or acetone cyanohydrin. Useful sources of sulfite are, for example, sulfurous acid, alkali metal sulfites, such as sodium sulfite or potassium sulfite, or alkali metal hydrogensulfites, for example sodium hydrogensulfite. Useful sulfinates are alkylsulfinates, such as sodium methylsulfinate, or arylsulfinates, such as sodium tolylsulfinate.

Suitable bases are, for example, nitrogen bases, such as triethylamine, pyridine, diazabicycloundecane (DBU) or dimethylaminopyridine (DMAP), alkali metal hydroxides, such as lithium hydroxide, sodium hydroxide or potassium hydroxide, alkaline earth metal hydroxides, such as barium hydroxide or calcium hydroxide, alkali metal carbonates, such as sodium carbonate or potassium carbonate, alkali metal bicarbonates, such as sodium bicarbonate or potassium bicarbonate, or alkali metal acetates, such as sodium acetate or potassium acetate.

The stoichiometric ratios are as follows: 1–5 equivalents of the nucleophilic ion which stabilizes a negative charge, preferably 1–2 equivalents, and, if appropriate, 1–5 equivalents of base, preferably 1–3 equivalents, are used per equivalent of the compound V. In certain cases, it may also be advantageous to use a catalytic amount of the nucleophilic ion which stabilizes a negative charge of 0.0001–10 mol %, preferably of 0,001–5 mol %. Work-up is carried out, for example, according to the following scheme: a) addition of water and extraction with an organic solvent, b) solvent exchange by distillative removal of the solvent, c) no purification; the solution is used directly in the next step.

This reaction is a process for converting a 2-halo alk-2-en-1-one into a 3-cyano alk-2-en-1-one, for example, if the nucleophilic ion Y⁻ which stabilizes a negative charge is the cyano group. However, Y⁻ may also be alkylsulfinate, arylsulfinate or sulfite. Reactions of 2-bromocycloalk-2-en-1-ones with NaCN or KCN are known from Tetrahedron Lett. 28 (1987), 6485–6488; Tetrahedron 43 (1987), 5593–5604.

Step e):

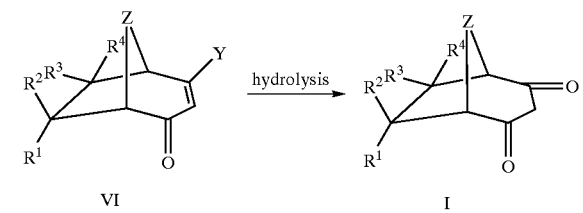

The reaction is carried out, for example, under the following conditions: suitable solvents are, for example, alcohols, such as methanol, ethanol, propanol or isopropanol, water, acetonitrile, dioxane or tetrahydrofuran, preferably methanol, ethanol and water. The hydrolysis can be initiated, for example, by alkali metal hydroxides, such as lithium hydroxide, sodium hydroxide or potassium hydroxide, alkaline earth metal hydroxides, such as calcium hydroxide or barium hydroxide, aluminum hydroxide, alkali metal carbonates, such as sodium carbonate or potassium carbonate, alkali metal bicarbonates, such as sodium bicarbonate or potassium bicarbonate, acetates, such as sodium acetate or potassium acetate, and nitrogen bases, such as triethylamine, pyridine or ammonia dissolved in water. However, it may also be advantageous to carry out the hydrolysis in acidic medium. Suitable acids are, for example, inorganic acids, for example hydrochloric acid, sulfuric acid, phosphoric acid, nitric acid, perchloric acid, chloric acid, hydrobromic acid and/or hydriodic acid, or organic acids, for example formic acid, acetic acid, propionic acid, butyric acid, stearic acid, oleic acid, benzoic acids and phenols. The reaction can be carried out at from −40° C. to 150° C., preferably at from room temperature to the reflux temperature of the solvent in question. The stoichiometric ratios are, for example, 1–5 equivalents, preferably 1–2 equivalents, of acid or base per equivalent of the compound VI.

Steps d) and e) can also be carried out as a one-pot reaction, using the reagent quantities stated in each case.

Compounds of the Formula VI where

X [sic] is cyano, sulfonate, $C_1$–$C_6$-alkylsulfonyl or unsubstituted or $C_1$–$C_3$-alkyl-, $C_1$–$C_3$-alkoxy-, $C_1$–$C_3$- alkylthio-, $C_1$–$C_3$-alkylsulfonyl-, halogen-, cyano-, nitro- or sulfonate-substituted phenylsulfonyl are novel.

PREPARATION EXAMPLES

Process Step a):

exo-3,4-Dichlorobicyclo[3.2.1]oct-2-ene.

Variant A:

At 50° C., aqueous sodium hydroxide solution (50%, 68 g, 0.85 mol) was slowly metered into a mixture of 2-norbornene (Aldrich, 99%, 20.0 g, 0.213 mol), chloroform (101.7 g, 0.85 mol), ethanol (2 ml) and benzyltrimethylammonium chloride (0.4 g, 0.0021 mol), and the mixture was then stirred at 50° C. for another 3 h. The mixture was poured onto ice-water and extracted with ethyl acetate. The organic phase was washed once with water, dried over sodium sulfate and evaporated to dryness.

Yield: 27.7 g (73.6%) $^1$H-NMR (270 MHz, CDCl$_3$) δ 6.18 (d, 1H); 4.22 (d, 1H); 2.80–2.60 (m, 2H); 2.10–1.32 (m, 6H).

Variant B:

At 50° C., aqueous sodium hydroxide solution (50%; 170 g, 2.13 mol) was added slowly to a mixture of 2-norbornene (Aldrich, 99%, 50.0 g, 0.53 mol), chloroform (254 g, 2.13 mol), ethanol (5 ml) and benzyltrimethylammonium chloride (1.3 g, 0.0053 mol). When about half of the aqueous sodium hydroxide solution had been metered in, a strong evolution of gas started. The mixture was stirred at 50° C. for another 4 h and cooled. The mixture was then partitioned between water and methyl tert-butyl ether, the organic phase was dried over sodium sulfate and the solvent was removed.

Yield: 22.4 g (23.4%) $^1$H-NMR (270 MHz, CDCl$_3$) δ 6.18 (d, 1H); 4.22 (d, 1H); 2.80–2.60 (m, 2H); 2.12–1.30 (m, 6H).

Variant C:

At 35–40° C., aqueous sodium hydroxide solution (50%, 163.6 g, 2.04 mol) was added dropwise with stirring, within 1 h, to a solution of 2-norbornene (Aldrich, 99%; 50.0 g, 0.53 mol) and benzyltrimethylammonium chloride (2.1 g, 0.011 mol) in chloroform (78.8 g, 0.66 mol) and dichloromethane (50 ml), and the mixture was stirred at 40° C. for 2 h. The mixture was cooled, diluted with water and extracted with dichloromethane. The organic phase was dried over sodium sulfate and concentrated.

Yield: 75.8 g (80.5%) $^1$H-NMR (270 MHz, CDCl$_3$) δ 6.18 (d, 1H), 4.22 (d, 1H); 2.81–2.60 (m, 2H); 2.10–1.32 (m, 6H). b.p.: 48–50° C. (0.5 mbar)

Process Step b):

Preparation of exo-3-chlorobicyclo[3.2.1]oct-3-en-2-ol.

Variant A:

A mixture of exo-3,4-dichlorobicyclo[3.2.1]oct-2-ene (75.8 g, 0.428 mol), water (700 ml), sodium hydroxide (68.5 g, 1.7 mol) and benzyltrimethylammonium chloride (0.1 g) was refluxed for 7 h. After cooling, the mixture was extracted with dichloromethane, the organic phase was dried over sodium sulfate and the solvent was removed.

Yield: 63.7 g (93.8%) of an orange oil $^1$H-NMR (270 MHz, CDCl$_3$) δ 6.12 (d, 1H); 3.76 (d, 1H); 2.56 (m, 2H); 2.26 (s, 1H); 2.00–2.58 (m, 4H); 1.40–1.24 (m, 2H).

Variant B:

At 35–45° C., aqueous sodium hydroxide solution (50%, 323.5 g, 4.04 mol) was added dropwise within 1.5 h to a mixture of 2-norbornene (Aldrich, 99%; 100 g, 1.06 mol), chloroform (152.6 g, 1.28 mol), dichloromethane (100 ml) and benzyltrimethylammonium chloride (4.2 g, 0.02 mol), and the mixture was stirred at 40° C. for another 1 h and at 55° C. for another 1 h. Water (1.0 l) was then added and, a little at a time, solid sodium hydroxide (100 g, 2.5 mol) was added. Low-boiling components were distilled off until the internal temperature of the flask reached 100° C. The mixture was then refluxed for another 5 h. After cooling, the mixture was extracted twice with dichloromethane, the organic phase was washed with water and dried over sodium sulfate, and the solvent was removed.

Yield: 119.3 g (71%) of an orange oil (GC 93.9%)

Process Step c):

Preparation of 3-chlorobicyclo[3.2.1]oct-3-en-2-one.

Variant A:

A solution of exo-3-chlorobicyclo[3.2.1]oct-3-en-2-ol (10.4 g, 0.066 mol) in chloroform (200 ml) was treated with manganese dioxide (MnO$_2$) (73.8 g, 0.72 mol) and stirred at room temperature for 4 days. Another 20 g of manganese dioxide were then added and the mixture was stirred at reflux temperature for another 8 h. The mixture was filtered off with suction through a depth filter and the filtrate was freed from the solvent.

Yield: 8.0 g (77.5%) b.p.: 80° C. (0.7 mbar) $^1$H-NMR (270 MHz, CDCl$_3$) δ 7.38 (d, 1H); 3.20 (d, 1H); 3.04 (d, 1H); 2.26-1.50 (m, 6H). $^{13}$C-NMR (90 MHz, CDCl$_3$) δ 195.4 (s); 152.0 (d); 131.0 (s); 50.2 (d); 40.1 (t); 38.6 (d); 29.1 (t); 24.2 (t).

Variant B:

At reflux temperature, air was passed through a solution of exo-3-chlorobicyclo[3.2.1]oct-3-en-2-ol (10.0 g, 0.063 mol) in dimethyl sulfoxide (80 ml) for 20 h. The mixture was allowed to cool and poured onto ice-water. The mixture was extracted with ethyl acetate and the organic phase was dried over sodium sulfate and concentrated.

Yield: 9.5 g $^1$H-NMR shows a mixture of about 60% product and 40% starting material.

Variant C:

At –60° C., a solution of dimethyl sulfoxide (33.1 g, 0.424 mol) in dichloromethane (70 ml) was added dropwise to a solution of oxalyl chloride (23.5 g, 0.194 mol) in dichloromethane (350 ml) and the mixture was stirred at –60° C. for another 30 min. At this temperature, a solution of exo-3-chlorobicyclo[3.2.1]oct-3-en-2-ol (32 g, 0.177 mol) in dichloromethane (140 ml) was then added dropwise. After a further 15 min, triethylamine (89.2 g, 0.88 mol) was finally added and the mixture was slowly warmed to room temperature. Water was added and then the pH was adjusted to 1 using 2N hydrochloric acid, the organic phase was dried over sodium sulfate and the solvent was removed. The residue was fractionated under reduced pressure.

Yield: 27.70 g (75.2%) b.p.: 80° C. (0.7 mbar) $^1$H-NMR (270 MHz, CDCl$_3$) δ 7.38 (d, 1H); 3.20 (d, 1H); 3.04 (d, 1H); 2.26–1.50 (m, 6H).

Variant D:

At –60° C., dimethyl sulfoxide (1.28 g, 0.016 mol) in dichloromethane (5 ml) was added dropwise to a solution of thionyl chloride (1.65 g, 0.0139 mol) in dichloromethane (25 ml). After 10 min, a solution of exo-3-chlorobicyclo [3.2.1]oct-3-en-2-ol (2.0 g, 0.0126 mol) in dichloromethane (10 ml) was added and the mixture was stirred at this temperature for another 15 min. At –60° C., triethylamine (6.4 g, 0.063 mol) was then metered in and the mixture was warmed slowly to room temperature. Water was added and the pH was adjusted to 1 using 2N hydrochloric acid. The organic phase was dried over sodium sulfate and concentrated.

Yield: 1.9 g (96.4%) $^1$H-NMR (270 MHz, CDCl$_3$) δ 7.38 (d, 1H); 3.20 (d, 1H); 3.04 (d, 1H); 2.26–1.50 (m, 6H).

Variant E:

A solution of thionyl chloride (1.65 g; 0.0139 mol) in dichloromethane (25 ml) was cooled to –20° C. and dimethyl sulfoxide (3.4 g, 0.044 mol) in dichloromethane (5 ml)

was added dropwise at this temperature. The mixture was stirred for 10 min and, at −20° C., a solution of exo-3-chlorobicyclo[3.2.1]oct-3-en-2-ol (2.0 g, 0.0126 mol) in dichloromethane (10 ml) was then added. After a further 15 min, triethylamine (6.4 g, 0.063 mol) was added and the mixture was warmed slowly to room temperature. Water was added and then the pH was adjusted to 1 using hydrochloric acid, the organic phase was dried over sodium sulfate and the solvent was removed.

Yield: 2.1 g (content according to GC 86.7%)

Variant F:

Phosphorus trichloride (1.91 g, 0.0139 mol) in dichloromethane (25 ml) was cooled to −30° C. and a solution of dimethyl sulfoxide (3.4 g, 0.044.mol) in dichloromethane (5 ml) was added dropwise. After 10 min, at a temperature of [lacuna], exo-3-chloro-bicyclo [3.2.1]oct-3-en-2-ol (2.0 g, 0.0126 mol) in dichloromethane (10 ml) was added and the mixture was stirred for another 15 min. The mixture was allowed to warm slowly to room temperature and the pH was adjusted to 1 using hydrochloric acid. The organic phase was separated off, dried with sodium sulfate and concentrated.

Yield: 2.2 g (content according to GC 84.3%)

Variant G:

At −30° C., a solution of dimethyl sulfoxide (3.4 g, 0.044 mol) in methylene chloride (5 ml) was added dropwise to a mixture of phosphorus oxychloride (2.1 g, 0.0139 mol) and methylene chloride (25 ml), and the mixture was stirred at this temperature for another 10 min. xo-3-Chlorobicyclo[3.2.1]oct-3-en-2-ol (2.0 g, 0.0126 mol) in dichloromethane (10 ml) was then added at −30° C. and the mixture was stirred for 15 min. Triethylamine (6.4 g, 0.063 mol) was added and then the mixture was warmed slowly to room temperature, water was added and the pH was adjusted to 1 using hydrochloric acid. The organic phase was separated off and dried over sodium sulfate, and the solvent was removed.

Yield: 2.1 g (content according to GC 88.3%)

Variant H:

At −60° C., DMSO (121 g, 1.55 mol) in dichloromethane (180 ml) was added dropwise to a solution of thionyl chloride (57.8 g, 0.486 mol) in dichloromethane (900 ml) and the mixture was stirred for another 10 min. At this temperature, exo-3-chlorobicyclo[3.2.1]oct-3-en-2-ol (70.0 g, 0.442 mol) in dichloromethane (360 ml) was then added and the mixture was stirred for another 10 min. Triethylamine (201 g, 1.99 mol) was added and then the mixture was stirred into cold hydrochloric acid and the organic phase was washed with water, dried over sodium sulfate and concentrated.

Yield: 71.2 g (GC 88.2%)

Process Step c) Bypassing Step b) by Direct Oxidation After Step a):

Preparation of 3-chlorobicyclo[3.2.1]oct-3-en-2-one

Variant A:

A mixture of exo-3,4-dichlorobicyclo[3.2.1]oct-2-ene (2.0 g, 0.011 mol), dimethyl sulfoxide (3.5 g, 0.045 mol) and sodium bicarbonate (1.0 g, 0.012 mol) was heated slowly to 150° C. and stirred at this temperature for 5 h. After cooling, water was added and the mixture was extracted with ethyl acetate. The organic phase was dried over sodium sulfate and concentrated.

Yield: 1.4 g

The $^1$H-NMR spectrum showed a mixture of about 85% of the desired product and about 15% of exo-3-chlorobicyclo[3.2.1]oct-3-en-2-ol (compound IV).

Variant B:

A mixture of exo-3,4-dichlorobicyclo[3.2.1]oct-2-ene (2.0 g, 0.011 mol), dimethyl sulfoxide (15 ml), dipotassium hydrogenphosphate (2.26 g, 0.013 mol), potassium dihydrogenphosphate (0.48 g, 0.004 mol) and sodium bromide (1.34 g, 0.013 mol) was refluxed for 6 h. After cooling, water was added and the mixture was extracted with ethyl acetate. The organic phase was washed with water, dried over sodium sulfate and concentrated.

Yield: 1.5 g

The $^1$H-NMR spectrum showed about 90% of product and 10% of exo-3-chlorobicyclo[3.2.1]oct-2-en-ol [sic].

Process Step d):

Preparation of 4-cyanobicyclo[3.2.1]oct-3-en-2-one.

Variant A:

A mixture of 3-chlorobicyclo[3.2.1]oct-3-en-2-one (0.5 g, 0.32 mmol), triethylamine (0.92 g, 0.32 mmol), acetone cyanohydrin (0.27 g, 0.32 mmol) and methanol (5 ml) was stirred at room temperature for 24 h, poured into water and extracted with ethyl acetate. The organic phase was washed with 2N hydrochloric acid, dried over sodium sulfate and concentrated.

Yield: 0.4 g (85%) $^1$H-NMR (400 MHz, CDCl$_3$) δ 6.40 (s, 1H); 3.08 (m, 2H); 2.30–2.05 (m, 3H); 1.94–1.86 (m, 1H); 1.82–1.72 (m, 1H); 1.66–1.58 (m, 1H). $^{13}$C-NMR (100 MHz, CDCl$_3$) δ 200.2 (s); 137.6 (s); 136.8 (d); 116.6 (s); 49.8 (d); 40.7 (d); 39.5 (d); 30.0 (t); 24.3 (t).

Variant B:

At room temperature, triethylamine (0.71 g, 7.03 mmol) was added dropwise to a mixture of 3-chlorobicyclo[3.2.1]oct-3-en-2-one (1.0 g, 6.39 mmol), potassium cyanide (0.42 g, 7.03 mmol), methyl tert-butyl ether (10 ml), water (1 ml) and a spatula-tipfull of tetrabutylammonium chloride, and the mixture was stirred at this temperature for 48 h. The mixture was poured into water and extracted with ethyl acetate. The organic phase was dried over sodium sulfate and concentrated.

Yield: 0.15 g (16%) $^1$H-NMR (270 MHz, CDCl$_3$) δ 6.40 (s, 1H); 3.08 (m, 2H); 2.30–2.05 (m, 3H); 1.94–1.58 (m, 3H).

Variant C:

At room temperature, triethylamine (0.71 g, 7.03 mmol) was added dropwise to a mixture of 3-chlorobicyclo[3.2.1]oct-3-en-2-one (1.0 g, 6.39 mmol), toluene (10 ml), potassium cyanide (0.42 g, 7.03 mmol), water (1 ml) and a spatula-tipfull of tetrabutylammonium chloride, and the mixture was stirred at this temperature for 48 h. Water was added and then the mixture was extracted with ethyl acetate and the organic phase was dried over sodium sulfate and concentrated.

Yield: 0.6 g (64%) $^1$H-NMR (270 MHz, CDCl$_3$) δ 6.40 (s, 1H); 3.08 (m, 2H); 2.30–2.05 (m, 3H); 1.94–1.58 (m, 3H).

Variant D:

Triethylamine (0.71 g, 7.03 mmol) was added dropwise to a mixture of 3-chlorobicyclo[3.2.1]oct-3-en-2-one (1.0 g, 6.39 mmol), dichloromethane (10 ml), potassium cyanide (0.42 g, 7.03 mmol), water (1 ml) and a spatula-tipfull of tetrabutylammonium chloride, and the mixture was stirred at room temperature for another 48 h. The mixture was poured into water, the organic phase was dried over sodium sulfate and the solvent was removed.

Yield: 0.9 g (96%) $^1$H-NMR (270 MHz, CDCl$_3$) δ 6.40 (s, 1H); 3.09 (m, 2H); 2.32–2.05 (m, 3H); 1.96–1.58 (m, 3H).

Process Step e):

Preparation of bicyclo[3.2.1]octane-2,4-dione

Variant A:

4-Cyanobicyclo[3.2.1]oct-3-en-2-one (0.02 g, 0.14 mmol) was treated with aqueous potassium hydroxide solution (0.5%, 20 mol) and stirred at room temperature for 2 h.

The mixture was acidified using hydrochloric acid and extracted with ethyl acetate. The organic phase was dried over sodium sulfate and concentrated.

Yield: 0.01 g (36%) $^1$H-NMR (270 MHz, CDCl$_3$): diketone form: δ 3.34 (d, 1H); 3.18 (d, 1H); 3.04 (s, 2H); 2.20–1.85 (m, 6H). Keto-enol form, resolved signals: δ 5.48 (s, 1H); 2.95 (s, 2H); 1.80–1.50 (m, 6H).

Variant B:

A mixture of 3-chlorobicyclo[3.2.1]oct-3-en-2-one (12.2 g, 0.078 mol), potassium cyanide (0.25 g, 0.0039 mol, 5 mol %) and methanol (100 ml) was treated with aqueous sodium hydroxide solution (50%, 21.8 g, 0.273 mol, 3.5 equivalents) and refluxed for 2 h. The solvent was then removed and the residue was taken up in dilute hydrochloric acid and extracted with ethyl acetate. The organic phase was dried over sodium sulfate and concentrated.

Yield: 9.6 g (89.2%) of a beige solid $^1$H-NMR (270 MHz, CDCl$_3$): diketone form δ 3.34 (d, 1H); 3.18 (d, 1H); 3.04 (s, 2H); 2.20–1.85 (m, 6H). Keto-enol form (resolved signals): δ 5.48 (s, 1H); 2.95 (s, 2H); 1.82–1.50 (m, 6H).

Variant C:

A solution of 3-chlorobicyclo[3.2.1]oct-3-en-2-one (30.0 g, 0.192 mol) and potassium cyanide (0.62 g, 9.6 mmol) in methanol (300 ml) was treated with aqueous sodium hydroxide solution (50%, 38.3 g, 0.48 mol) and refluxed for 4 h. The solvent was removed and the residue was taken up in water and extracted with dichloromethane. The aqueous phase was adjusted to pH 1 using hydrochloric acid and extracted with dichloromethane, and the solvent was removed.

Yield: 20.3 g (77%) GC 95.4%

We claim:

1. A process for preparing bicyclic 1,3-diketones of the formula I

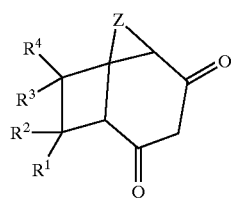

where $R^1$, $R^2$, $R^3$ and $R^4$ are hydrogen, $C_1$–$C_4$-alkyl, $C_1$–$C_4$-alkoxycarbonyl, halogen, cyano, nitro, $C_1$–$C_4$-alkylthio, $C_1$–$C_4$-alkylsulfenyl or $C_1$–$C_4$-alkylsulfonyl and Z is $C_1$–$C_4$-alkylene, O, S, N—$R^5$ where $R^5$ is $C_1$–$C_4$-alkyl or $C_1$–$C_4$-alkylcarbonyl, which comprises a) reacting a bicyclic olefin of the formula II with haloform in the presence of a base to give the ring-expanded product of the formula III

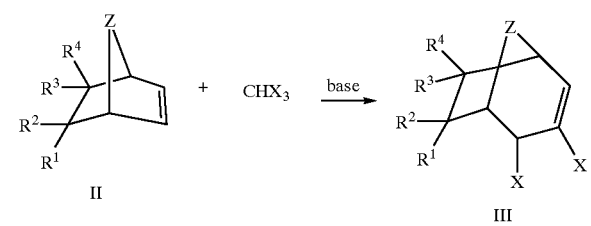

where $R^1$–$R^4$ and Z are as defined above and

X is halogen;

b) hydrolyzing the allylic halogen of the compound of the formula III to the allyl alcohol of the formula IV

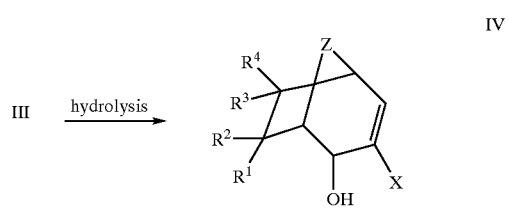

c) oxidizing the allyl alcohol of the formula IV to the unsaturated ketone of the formula V

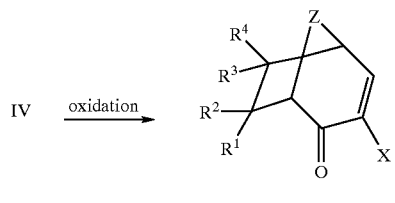

d) reacting the ketone of the formula V with a nucleophilic ion Y$^-$ which stabilizes a negative charge to give the ketone of the formula VI

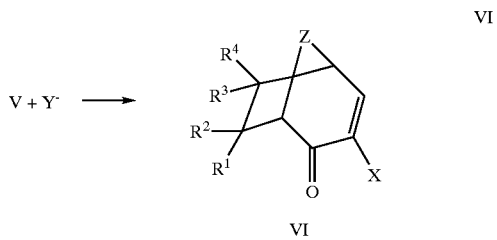

wherein Y is the nucleophilic group of the nucleophilic ion Y$^-$, e) hydrolyzing the ketone of the formula VI to the bicyclic 1,3-diketone of the formula I.

2. A process as claimed in claim 1, wherein the hydrolysis step b) is bypassed and the allylic halogen of the compound of the formula III is oxidized to the unsaturated ketone of the formula V

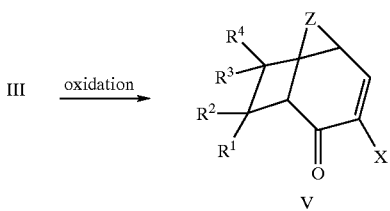

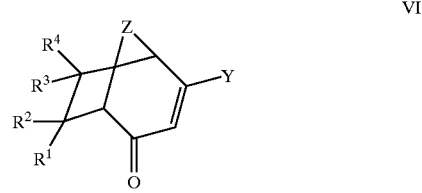

where $R^1$–$R^4$, Z and X are as defined in claim 1.

3. A process as claimed in either of claims 1 and 2, wherein the haloform used in step a) is chloroform.

4. A process as claimed in any of claims 1 to 3, wherein the base used in step a) is an alkali metal hydroxide, an alkali metal alkoxide, an alkali metal amide or an organometallic compound.

5. A process as claimed in claim 4, wherein the organometallic compound used is a Grignard reagent or $C_1$–$C_4$-alkyllithium.

6. A process as claimed in claim 1, wherein the hydrolysis in step b) is carried out in water, alcohol or ether.

7. A process as claimed in claim 6, wherein the hydrolysis in step b) is carried out in the presence of an alkali metal hydroxide.

8. A process as claimed in claim 1, wherein the oxidation in step c) is carried out using oxidizing agents selected from the group consisting of metal oxides, peroxides, perhalogenates, halogenates, hypohalogenites, NBS, NCS, DMSO, halogen, air, amine oxides and mixtures thereof.

9. A process as claimed in claim 2, wherein the oxidation of the allylic halogen of the compound of the formula III is carried out using oxidizing agents selected from the group consisting of metal oxides, peroxides, perhalogenates, halogenates, hypohalogenites, NBS, NCS, DMSO, halogen, air, amine oxides and mixtures thereof.

10. A process as claimed in claim 1, wherein, in step d), the ketone of the formula V is reacted with a nucleophilic ion $Y^-$ which stabilizes a negative charge and is selected from the group consisting of cyanides, sulfites, $C_1$–$C_6$-alkylsulfinates and unsubstituted or $C_1$–$C_3$-alkyl-, $C_1$–$C_3$-alkoxy-, $C_1$–$C_3$-alkylthio-, $C_1$–$C_3$-alkylsulfonyl-, halogen-, cyano-, nitro- or sulfonate-substituted phenylsulfinate and mixtures thereof.

11. A process as claimed in claim 10, wherein the ketone and the nucleophilic ion $Y^-$ which stabilizes a negative charge are reacted in an equivalence ratio of 1:5.

12. A process as claimed in claim 1, wherein the hydrolysis of the ketone of the formula IV to the diketone of the formula I in step e) is carried out in the presence of an alkali metal hydroxide or alkaline earth metal hydroxide.

13. A process as claimed in claim 1, wherein the reaction of the ketone of the formula V with a nucleophilic ion $Y^-$ to give the ketone of the formula VI is carried out without intermediate isolation with direct hydrolysis to give the diketone of the formula I.

14. A bicyclic ketone of the formula VI as claimed in claim 1, where
$R^1$, $R^2$, $R^3$ and $R^4$ are hydrogen, $C_1$–$C_4$-alkyl, $C_1$–$C_4$-alkoxycarbonyl, halogen, cyano, nitro, $C_1$–$C_4$-alkylthio, $C_1$–$C_4$-alkylsulfenyl or $C_1$–$C_4$-alkylsulfonyl and Z is $C_1$–$C_4$-alkylene, O, S, N—$R^5$ where
$R^5$ is $C_1$–$C_4$-alkyl or $C_1$–$C_4$-alkylcarbonyl, Y is cyano, sulfonate, $C_1$–$C_6$-alkylsulfonyl or unsubstituted or $C_1$–$C_3$-alkyl-, $C_1$–$C_3$-alkoxy-, $C_1$–$C_3$-alkylthio-, $C_1$–$C_3$-alkylsulfonyl-, halogen-, cyano-, nitro- or sulfonate-substituted phenylsulfonyl.

15. A bicyclic ketone of the formula VI as claimed in claim 14, where
Y is cyano.

16. A bicyclic ketone as claimed in claim 14, where
Z is $C_1$–$C_4$-alkylene or O.

17. A bicyclic ketone as claimed in claim 16, where
Z is $C_1$–$C_4$-alkylene.

18. A bicyclic ketone as claimed in claim 14, where
$R^1$, $R^2$, $R^3$ and $R^4$ are hydrogen.

19. A bicyclic ketone as claimed in claim 14, where
$R^1$, $R^2$, $R^3$ and $R^4$ are hydrogen,
Z is methylene and
Y is cyano.

* * * * *